US011806270B2

(12) United States Patent
Tsai et al.

(10) Patent No.: US 11,806,270 B2
(45) Date of Patent: *Nov. 7, 2023

(54) HIGH BARRIER ELASTOMER FECAL CATHETER OR OSTOMY POUCH

(71) Applicant: ConvaTec Technologies Inc., Las Vegas, NV (US)

(72) Inventors: Mingliang Lawrence Tsai, Holmdel, NJ (US); Tinh Nguyen-Demary, Bridgewater, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 38 days.

This patent is subject to a terminal disclaimer.

(21) Appl. No.: 17/534,550

(22) Filed: Nov. 24, 2021

(65) Prior Publication Data
US 2022/0087850 A1    Mar. 24, 2022

Related U.S. Application Data

(63) Continuation of application No. 16/186,003, filed on Nov. 9, 2018, now Pat. No. 11,191,661, which is a continuation of application No. 14/005,814, filed as application No. PCT/US2012/029375 on Mar. 16, 2012, now Pat. No. 10,166,137.

(60) Provisional application No. 61/453,667, filed on Mar. 17, 2011.

(51) Int. Cl.
| | |
|---|---|
| *A61F 5/441* | (2006.01) |
| *A61F 5/445* | (2006.01) |
| *A61L 28/00* | (2006.01) |
| *A61L 29/02* | (2006.01) |
| *A61L 29/04* | (2006.01) |
| *A61L 29/08* | (2006.01) |
| *A61L 29/12* | (2006.01) |
| *A61L 29/14* | (2006.01) |

(52) U.S. Cl.
CPC .............. *A61F 5/441* (2013.01); *A61F 5/445* (2013.01); *A61L 28/003* (2013.01); *A61L 28/0026* (2013.01); *A61L 28/0069* (2013.01); *A61L 28/0092* (2013.01); *A61L 29/02* (2013.01); *A61L 29/049* (2013.01); *A61L 29/085* (2013.01); *A61L 29/126* (2013.01); *A61L 29/14* (2013.01); *A61L 2300/64* (2013.01); *A61L 2400/12* (2013.01); *A61L 2420/04* (2013.01)

(58) Field of Classification Search
CPC ........ A61L 29/049; A61L 29/14; A61L 29/02; A61L 28/0026; A61L 28/003; A61L 28/0069; A61L 29/085; A61L 29/126; A61L 28/0092; A61L 2420/04; A61L 2300/64; A61L 2400/12
See application file for complete search history.

(56) References Cited

U.S. PATENT DOCUMENTS

| | | | | |
|---|---|---|---|---|
| 4,546,143 A | * | 10/1985 | Weil ........................ | C08L 21/00 524/511 |
| 5,019,062 A | * | 5/1991 | Ryan ................... | A61F 13/5123 428/323 |
| 5,306,487 A | * | 4/1994 | Karapasha .............. | A61L 15/18 604/359 |
| 5,817,300 A | * | 10/1998 | Cook ...................... | A61Q 15/00 424/76.8 |
| 5,860,959 A | * | 1/1999 | Gent ...................... | A61F 5/441 604/327 |
| 6,329,465 B1 | * | 12/2001 | Takahashi .............. | H01B 3/441 525/240 |
| 6,485,476 B1 | * | 11/2002 | von Dyck ............... | A61F 5/441 604/332 |
| 6,605,304 B1 | * | 8/2003 | Wellinghoff ......... | C11D 3/0052 424/44 |
| 6,617,016 B2 | * | 9/2003 | Zhang .................... | C08L 53/025 428/318.6 |
| 6,852,100 B1 | * | 2/2005 | Gent ...................... | A61F 5/441 604/333 |
| 6,946,182 B1 | * | 9/2005 | Allgeuer ................. | B29C 59/04 428/172 |
| 6,946,522 B2 | * | 9/2005 | Jacob ..................... | C08L 53/025 525/240 |
| 7,056,971 B2 | * | 6/2006 | Varma ................ | B65D 41/0442 525/62 |
| 7,060,753 B2 | * | 6/2006 | Jacob ................... | C08K 5/0008 525/200 |

(Continued)

FOREIGN PATENT DOCUMENTS

| | | |
|---|---|---|
| EP | 3001976 A1 | 4/2016 |
| EP | 3100758 A1 | 12/2016 |
| EP | 3315159 A1 | 5/2018 |
| EP | 3351208 A1 | 7/2018 |
| WO | 0134685 A1 | 5/2001 |
| WO | 2007106671 A1 | 9/2007 |
| WO | 2008052018 A2 | 5/2008 |
| WO | 2009048375 A1 | 4/2009 |
| WO | 2018134591 A1 | 7/2018 |
| WO | 2018143487 A1 | 8/2018 |
| WO | 2019014344 A1 | 1/2019 |

(Continued)

OTHER PUBLICATIONS

Extended European Search Report; European Patent Office; European Patent Application No. 19218078.4; dated Apr. 21, 2020; 10 pages.

(Continued)

*Primary Examiner* — Guy K Townsend
(74) *Attorney, Agent, or Firm* — Taft Stettinius & Hollister LLP; Ryan O. White; Derek B. Lavender

(57) ABSTRACT

Certain embodiments relate to a soft odor barrier material in a medical device. The soft odor barrier material includes an elastomer and an antiblocking agent. In certain forms, the antiblocking agent imparts an interior rough surface having an arithmetic mean surface roughness (Ra) not less than 0.1 μm. In certain forms, the antiblocking agent is non-blocking upon folding and packaging.

20 Claims, No Drawings

(56) References Cited

U.S. PATENT DOCUMENTS

| | | | |
|---|---|---|---|
| 7,629,406 B2* | 12/2009 | Qian | C08L 23/06 |
| | | | 524/445 |
| 8,323,254 B2* | 12/2012 | Tsai | B32B 7/12 |
| | | | 604/93.01 |
| 10,166,137 B2* | 1/2019 | Nguyen-Demary | A61F 5/441 |
| 10,207,076 B2 | 2/2019 | Foley et al. | |
| 10,322,024 B2* | 6/2019 | Chang | B32B 27/08 |
| 10,426,584 B2 | 10/2019 | McClurg | |
| 10,426,654 B2 | 10/2019 | Ugarte | |
| 10,426,918 B2 | 10/2019 | Foley et al. | |
| 10,426,919 B2 | 10/2019 | Erbey, II et al. | |
| 10,434,282 B2 | 10/2019 | Kearns et al. | |
| 10,441,454 B2 | 10/2019 | Tanghoej et al. | |
| 10,449,083 B2 | 10/2019 | Pierson | |
| 10,449,327 B2 | 10/2019 | Overtoom | |
| 10,449,328 B2 | 10/2019 | Tanghoej et al. | |
| 10,449,329 B2 | 10/2019 | Foley et al. | |
| 10,463,466 B2 | 11/2019 | Cullison | |
| 10,463,833 B2 | 11/2019 | Clarke et al. | |
| 10,470,861 B2 | 11/2019 | Khamis et al. | |
| 10,485,483 B1 | 11/2019 | Brody | |
| 10,485,644 B2 | 11/2019 | Orr et al. | |
| 10,493,230 B2 | 12/2019 | Guldager et al. | |
| 10,493,231 B2 | 12/2019 | McMenamin et al. | |
| 10,493,252 B2 | 12/2019 | Browne et al. | |
| 10,506,965 B2 | 12/2019 | Cooper et al. | |
| 10,512,713 B2 | 12/2019 | Erbey, II et al. | |
| 10,531,894 B2 | 1/2020 | Connors et al. | |
| 10,531,976 B2 | 1/2020 | Palmer | |
| 10,548,523 B2 | 2/2020 | Ahmadi et al. | |
| 10,569,046 B2 | 2/2020 | Steindahl et al. | |
| 10,569,047 B2 | 2/2020 | Farrell et al. | |
| 10,569,051 B2 | 2/2020 | Conway et al. | |
| 10,575,935 B2 | 3/2020 | Wei et al. | |
| 10,588,774 B2 | 3/2020 | Alhaqqan | |
| 10,589,061 B2 | 3/2020 | Palmer | |
| 10,589,093 B2 | 3/2020 | Imran | |
| 10,610,344 B2 | 4/2020 | Shapiro et al. | |
| 10,610,664 B2 | 4/2020 | Erbey, II et al. | |
| 10,617,843 B2 | 4/2020 | Paz | |
| 10,631,788 B2 | 4/2020 | Brody | |
| 10,639,451 B2 | 5/2020 | Kearns et al. | |
| 10,639,452 B2 | 5/2020 | Linares et al. | |
| 10,646,688 B2 | 5/2020 | Hannon et al. | |
| 10,667,894 B2 | 6/2020 | Forsell | |
| 10,668,249 B2 | 6/2020 | Douglas et al. | |
| 10,675,134 B2 | 6/2020 | Herrera et al. | |
| 10,675,435 B2 | 6/2020 | Herrera et al. | |
| 10,682,214 B2 | 6/2020 | Sufyan et al. | |
| 10,690,655 B2 | 6/2020 | Duval | |
| 10,702,671 B2 | 7/2020 | Terry | |
| 10,709,819 B2 | 7/2020 | Littleton et al. | |
| D893,706 S | 8/2020 | Lessmann | |
| 10,736,491 B2 | 8/2020 | Truckai | |
| 10,737,057 B1 | 8/2020 | Mikhail et al. | |
| 10,744,298 B1 | 8/2020 | Bello et al. | |
| 10,751,493 B2 | 8/2020 | Gregory et al. | |
| 10,758,704 B2 | 9/2020 | Hickmott et al. | |
| 10,765,833 B2 | 9/2020 | Kearns | |
| 10,765,834 B2 | 9/2020 | Erbey, II et al. | |
| 10,772,755 B2 | 9/2020 | Gregory | |
| 10,780,243 B2 | 9/2020 | Reyes | |
| 10,780,244 B2 | 9/2020 | Conway et al. | |
| 10,780,245 B2 | 9/2020 | Schonfeldt | |
| 10,807,287 B2 | 10/2020 | Rolsted et al. | |
| 10,814,097 B2 | 10/2020 | Palmer | |
| 11,191,661 B2* | 12/2021 | Tsai | A61L 29/126 |
| 11,351,054 B2* | 6/2022 | Chang | B32B 5/32 |
| 2002/0055594 A1* | 5/2002 | Roux | B01J 20/28014 |
| | | | 525/329.7 |
| 2002/0119301 A1* | 8/2002 | Zhang | C08L 53/02 |
| | | | 428/318.6 |
| 2003/0018293 A1 | 1/2003 | Tanghoj et al. | |
| 2005/0043715 A1 | 2/2005 | Nestenborg et al. | |
| 2006/0163097 A1 | 7/2006 | Murray et al. | |
| 2006/0173430 A1* | 8/2006 | Lee | A61F 13/00 |
| | | | 604/360 |
| 2007/0237916 A1* | 10/2007 | Rasmussen | A61F 5/441 |
| | | | 428/521 |
| 2008/0103463 A1* | 5/2008 | Tsai | B29C 63/42 |
| | | | 604/317 |
| 2009/0088711 A1* | 4/2009 | Shelley | A61M 1/84 |
| | | | 604/328 |
| 2009/0137985 A1 | 5/2009 | Tanghoej et al. | |
| 2009/0216207 A1* | 8/2009 | Nielsen | C08J 5/18 |
| | | | 428/220 |
| 2010/0324535 A1 | 12/2010 | Triel | |
| 2011/0052737 A1* | 3/2011 | Florence | A61Q 19/007 |
| | | | 424/774 |
| 2011/0190736 A1 | 8/2011 | Young et al. | |
| 2011/0224653 A1 | 9/2011 | Torstensen | |
| 2013/0138135 A1 | 5/2013 | Rosen et al. | |
| 2013/0161208 A1 | 6/2013 | Gustavsson | |
| 2013/0161227 A1 | 6/2013 | Gustavsson | |
| 2013/0261608 A1 | 10/2013 | Tanghoj et al. | |
| 2014/0066905 A1 | 3/2014 | Young | |
| 2014/0207094 A1* | 7/2014 | Chang | B32B 27/302 |
| | | | 604/339 |
| 2014/0288517 A1* | 9/2014 | Tsai | A61L 28/0026 |
| | | | 604/333 |
| 2014/0336569 A1 | 11/2014 | Gobel | |
| 2014/0378951 A1 | 12/2014 | Dye | |
| 2015/0133898 A1 | 5/2015 | Murray et al. | |
| 2015/0273180 A1 | 10/2015 | Schonfeldt | |
| 2015/0273747 A1 | 10/2015 | Montes de Oca Balderas et al. | |
| 2015/0290421 A1 | 10/2015 | Glickman et al. | |
| 2015/0297862 A1 | 10/2015 | Sadik et al. | |
| 2015/0320970 A1 | 11/2015 | Foley et al. | |
| 2016/0067445 A1 | 3/2016 | Murray et al. | |
| 2016/0184551 A1 | 6/2016 | Nyman et al. | |
| 2016/0206469 A1 | 7/2016 | Prezelin | |
| 2016/0287759 A1 | 10/2016 | Clarke et al. | |
| 2016/0317715 A1 | 11/2016 | Rostami et al. | |
| 2016/0325903 A1 | 11/2016 | Doerschner et al. | |
| 2017/0000978 A1 | 1/2017 | Murray et al. | |
| 2017/0021128 A1 | 1/2017 | Erbey, II et al. | |
| 2017/0105826 A1 | 4/2017 | Erikstrup | |
| 2017/0348137 A1 | 12/2017 | Hvid et al. | |
| 2017/0348138 A1 | 12/2017 | Hvid et al. | |
| 2018/0015250 A1 | 1/2018 | Tsukada et al. | |
| 2018/0021481 A1 | 1/2018 | Yin et al. | |
| 2018/0050173 A1 | 2/2018 | Kearns | |
| 2018/0071482 A1 | 3/2018 | Fitzpatrick et al. | |
| 2018/0369474 A1 | 12/2018 | Falleboe et al. | |
| 2019/0099583 A1 | 4/2019 | Charles et al. | |
| 2019/0151134 A1* | 5/2019 | Tsai | A61L 28/003 |
| 2019/0224402 A1 | 7/2019 | Henry et al. | |
| 2019/0231581 A1* | 8/2019 | Chang | B32B 5/32 |
| 2019/0240060 A1 | 8/2019 | He et al. | |
| 2019/0247549 A1 | 8/2019 | Nielsen | |
| 2019/0314044 A1 | 10/2019 | Long et al. | |
| 2019/0314188 A1 | 10/2019 | Barrientos | |
| 2019/0314190 A1 | 10/2019 | Sanchez et al. | |
| 2019/0321587 A1 | 10/2019 | McMenamin et al. | |
| 2019/0321589 A1 | 10/2019 | Bonneau | |
| 2019/0358075 A1 | 11/2019 | Scharich, III et al. | |
| 2019/0358435 A1 | 11/2019 | Andersin et al. | |
| 2019/0365561 A1 | 12/2019 | Newton et al. | |
| 2019/0366038 A1 | 12/2019 | Denman et al. | |
| 2019/0374324 A1 | 12/2019 | Luleci | |
| 2019/0381291 A1 | 12/2019 | Feld | |
| 2019/0388659 A1 | 12/2019 | Ruel | |
| 2020/0001045 A1 | 1/2020 | McIntyre | |
| 2020/0001049 A1 | 1/2020 | House | |
| 2020/0016380 A1 | 1/2020 | Murray et al. | |
| 2020/0022636 A1 | 1/2020 | Suehara et al. | |
| 2020/0030135 A1 | 1/2020 | Woodyard | |
| 2020/0030582 A1 | 1/2020 | Dong | |
| 2020/0030595 A1 | 1/2020 | Boukidjian et al. | |
| 2020/0037832 A1 | 2/2020 | Wang et al. | |
| 2020/0054800 A1 | 2/2020 | Wilbourn et al. | |
| 2020/0094017 A1 | 3/2020 | Erbey, II et al. | |
| 2020/0101280 A1 | 4/2020 | Peddicord | |

(56) References Cited

U.S. PATENT DOCUMENTS

| | | |
|---|---|---|
| 2020/0129731 A1 | 4/2020 | Brar et al. |
| 2020/0139109 A1 | 5/2020 | Imran |
| 2020/0146799 A1 | 5/2020 | Connors et al. |
| 2020/0146871 A1 | 5/2020 | Palmer |
| 2020/0163543 A1 | 5/2020 | Schutt et al. |
| 2020/0163699 A1 | 5/2020 | Bacich et al. |
| 2020/0179644 A1 | 6/2020 | Gukdbaek |
| 2020/0179665 A1 | 6/2020 | Orr et al. |
| 2020/0188631 A1 | 6/2020 | Hannon et al. |
| 2020/0206389 A1 | 7/2020 | Vange |
| 2020/0206411 A1 | 7/2020 | Henry et al. |
| 2020/0206470 A1 | 7/2020 | Orr et al. |
| 2020/0215303 A1 | 7/2020 | Erbey, II et al. |
| 2020/0222220 A1 | 7/2020 | Kappus et al. |
| 2020/0222659 A1 | 7/2020 | Schertiger et al. |
| 2020/0222660 A1 | 7/2020 | Erbery, II et al. |
| 2020/0222674 A1 | 7/2020 | Inoue et al. |
| 2020/0230349 A1 | 7/2020 | McMenamin et al. |
| 2020/0230382 A1 | 7/2020 | Siebert |
| 2020/0246587 A1 | 8/2020 | Tal et al. |
| 2020/0254215 A1 | 8/2020 | Portela et al. |
| 2020/0261692 A1 | 8/2020 | Palmer |
| 2020/0262868 A1 | 8/2020 | Ricca et al. |
| 2020/0268947 A1 | 8/2020 | Erbey, II et al. |
| 2020/0276410 A1 | 9/2020 | Son |
| 2020/0282092 A1 | 9/2020 | Paul et al. |
| 2020/0330724 A1 | 10/2020 | Mikhail et al. |
| 2022/0087850 A1* | 3/2022 | Tsai .................. A61L 28/0026 |

FOREIGN PATENT DOCUMENTS

| | | |
|---|---|---|
| WO | 2019038732 A1 | 2/2019 |
| WO | 2019038734 A1 | 2/2019 |
| WO | 2019106581 A2 | 6/2019 |
| WO | 2019123004 A1 | 6/2019 |
| WO | 2019184222 A1 | 10/2019 |
| WO | 2019222644 A1 | 11/2019 |
| WO | 2019229597 A1 | 12/2019 |
| WO | 2020015804 A1 | 1/2020 |

OTHER PUBLICATIONS

Chinese Office Action; China Patent Office; Chinese Patent Application No. 201810218760.8; dated Aug. 14, 2020; 19 pages.

* cited by examiner

HIGH BARRIER ELASTOMER FECAL CATHETER OR OSTOMY POUCH

CROSS-REFERENCE TO RELATED APPLICATIONS

The present application is a Continuation of U.S. patent application Ser. No. 16/186,003, filed on 9 Nov. 2018, which is a Continuation of U.S. patent application Ser. No. 14/005,814, filed on 26 Mar. 2014 (now U.S. Pat. No. 10,166,137), which is a national stage entry of International PCT Application No. PCT/US12/29375, filed on 16 Mar. 2012, which claims the benefit of U.S. Provisional Patent Application No. 61/453,667, filed on 17 Mar. 2011, the contents of each of which applications are incorporated herein by reference in their entirety.

FIELD OF THE INVENTION

The present invention relates to an odor barrier material for a fecal catheter, a fecal pouch, or an ostomy pouch.

BACKGROUND OF THE INVENTION

Fecal catheters have occasionally been criticized for the transmission of fecal odor through the tubular walls.

A possible cause of the poor odor barrier is the silicone material of which these devices are composed. The odor barrier of silicone is known to be one of the worst among polymer materials. For example, the oxygen transmission rate of silicone has been reported to be 775,000 cc mil/m$^2$/day. Therefore, a 20 mil thick silicone catheter is about 3 orders of magnitude worse than a commonly used ostomy film having a transmission rate of 50 cc/m$^2$/day or less.

Another possible explanation for silicone fecal catheter having poor odor barrier is that the extruded silicone utilized in such devices is relatively rough and as a result could trap fecal components. The contours of the spots trapping the fecal material provide substantial surface area, through which odor is transmitted.

The combination of high odor transmission rate and large surface area contributes to the poor odor barrier characteristics of the silicone used in fecal catheters.

It would be desirable to develop a material to be used in a fecal catheter that has the desirable characteristics of silicone while providing an odor barrier substantially better than that of silicone.

It is the object of the present invention to provide an odor barrier polymer having these characteristics.

DESCRIPTION OF THE INVENTION

Thermoplastic elastomer (TPE) or curable elastomer is well known for use in medical devices. However, these elastomers are not known to exhibit high odor barrier properties. The present invention is the modification of elastomer to achieve a high odor barrier while maintaining its softness, ability for post extrusion converting (welding and bonding) and non-blocking characteristics.

One embodiment of the present invention related to single layer of catheter made from a high barrier elastomer such that the odor barrier measured by oxygen transmission rate per ASTM D3985 is not more than 50,000 cc mil/m$^2$/day at 23° C., or more preferably not more than 5,000 cc mil/m$^2$/day. Such a catheter is at least 10 times better in odor barrier than the silicone catheter.

U.S. Pat. Nos. 6,946,522, 7,056,971, and 7,060,753 disclosed the use of a liquid polyisobutene oil plasticizer to improve the gas barrier of the TPE. However, these formulations, especially when targeting a soft elastomer, i.e., Shore A less than 60, creates a blocking issue in which the surface of TPE catheter seals against each other upon folding and packaging. The use of a higher amount of oil plasticizer would allow a softer TPE, but it comes with an adverse effect in an oily surface, resulting in poor post-extrusion converting (welding and bonding). In addition, the TPE based on an olefin block copolymer (OBC, such as Infuse™ made by Dow) was not disclosed. Although common approaches exist to minimize the blocking, including adding mineral oil or slip additives. These approaches; however, have drawbacks in that they prevent the parts from being further converted into a fecal catheter due to their adverse effects on the surface bonding. U.S. Pat. No. 7,629,406 disclosed the use of an organoclay at a concentration less than 4% to improve the barrier properties of high density polyethylene (HDPE). However, the use of organoclay in a TPE was not mentioned with a Shore A hardness not more than 60, or preferably not more than 50.

Another embodiment of the present invention is related to a fecal catheter, having a Shore A hardness not more than 60 and an oxygen transmission rate not more than 2,500 cc/m$^2$/day or preferably not more than 1,000 cc/m$^2$/day, comprising (1) a thermoplastic elastomer, (2) odor barrier modifier, and (3) an antiblocking agent of at least 0.1%, wherein thermoplastic elastomer is selected from the group consisting of a styrenic block copolymer, a thermoplastic vulcanizate, or a polyolefin elastomer, and wherein odor barrier modifier is selected from the group consisting of polyisobutene, polybutene, or an organoclay, and wherein the antiblocking agent is selected from the group consisting of an essentially inorganic fillers, such as silica, talc, clay, mica, etc. and blends thereof. It is noted organoclays can be used in one embodiment as both the odor barrier modifier and as the antiblocking agent. Organoclays include montmorillonite clay, smectite clay, intercalated clay, nanoclay, or a mixture of above. Organoclay described in this invention includes montmorillonite clay, made by Nanocor, which is the most common member of the smectite clay family. Organoclay may consist of nanoclay with a unique morphology such that one dimension is in the nanometer range. In addition, organoclay is preferred to be intercalated with an organic intercalant resulting in a clay-chemical complex wherein the clay gallery spacing has increased due to the process of surface modification. Under the proper conditions of temperature and shear, an intercalate is capable of exfoliating in a resin matrix. Optionally, the following additives can be used to facilitate the manufacturing of catheter extrusion, including melt viscosity modifier, tackifier, detackifier, plasticizer, etc.

Styrenic block copolymer (SBC) based thermoplastic elastomer includes styrene-isoprene-styrene (SIS), styrene-butadiene-styrene (SBS), styrene-ethylene/butylene-styrene (SEBS), styrene-ethylene/propylene-styrene (SEPS), and blends thereof. Thermoplastic vulcanizate (TPV) includes a blend of curable rubber and a polyolefin (i.e., PP or PE, homopolymers and copolymers). Curable rubbers include EPDM, EP rubber, santoprene, etc. A polyolefin elastomer includes an olefin block copolymer (OBC), such as Infuse made by Dow, where a crystalline phase of a olefin block copolymer acted as hard blocks, and the amorphous block copolymer acted as soft blocks within the same polymer matrix. The following is a summary of odor barrier as measured by oxygen transmission rate at 23° C. per ASTM D3985:

TABLE 1

Odor Barrier Comparison of Various Elastomers without Organoclays or zeolites

|  | Silicone | SBC | TPV | OBC | SBC w/polyisobutene | SBC w/polyisobutene and Organoclay |
|---|---|---|---|---|---|---|
| OTR, cc/m²/day, 20 mil thick wall, ASTM D3985 | 37,500 | 2.500-4.500 | 2,500 | 2,500 | 1,000 | 250 |
| Onion Barrier, ISO 8670-3 | Very poor, detectable in 10 minutes | Poor, detectable in 60 minutes | Poor, detectable in 60 minutes | Poor, detectable in 60 minutes | Better, detectable in 120 minutes | Good, not detectable for 8 hrs |

When antiblocking agent, at least 0.1% or more preferably more than 0.5%, was added to a high barrier elastomer formulation containing a SBC thermoplastic elastomer and a liquid polyisobutene, an odor barrier in the range of around 1000 cc/m²/day was achieved for making a non-blocking fecal catheter. This level of odor barrier improvement was confirmed by an onion test per ISO 8670-3 such that the onion odor breakthrough was longer than 120 minutes. Additional barrier improvement was seen in fecal catheter made from PTE containing a SBC thermoplastic elastomer, a liquid polyisobutene, an organoclay. In this example, onion odor breakthrough was longer than 8 hours. The results of both oxygen barrier and onion barrier were shown in Table 1.

Another embodiment of the present invention is a fecal catheter based on a multilayer structure, wherein at least one layer is selected from a high barrier elastomer described above without any antiblocking agent, and at least another skin layer is selected from the group consisting of (1) same high barrier elastomer described above with at least 0.1% of antiblocking agent, or an elastomer alloy with or without the use of antiblocking agent. An elastomer alloy is defined as a blend of two polymer matrixes which are incompatible in a molecular level. The advantage of antiblocking agent is to impart a rough surface so that the catheter is not blocking. The advantage of an elastomer alloy is that the incompatibility in a molecular level creates a roughness on the catheter surface, giving rise to a non-blocking catheter. In addition, common materials to add for an elastomer alloy include, but not limited to, thermoplastic polyurethane (TPU). Due to a more polar structure in TPU, the subsequent converting of an elastomer alloy is easier. Since the majority of the catheter structure is provided by a high barrier elastomer, the odor barrier and the softness is maintained based on the disclosure above. Because both the center layer and the skin layer are elastomers based, the adhesion between the layers of a fecal catheter is sufficiently good.

Besides the addition of anti-blocking agent, cold processing conditions can be utilized to enhance a rough surface of the catheter wall so that the catheter is not blocking. The effect of anti-blocking agent and/or cold processing conditions is a rough surface that could be characterized by surface roughness using a non-contact surface structure analyzer, such as Scanning White Light interferometry (SWLI), Atomic Force Microscopy (AFM), etc. A non-contact imaging surface structure analyzer based on SWLI is made by Zygo NewView 7300. A non-contact atomic force microscopy can be made by FEI. A typical parameter that has been used to quantify the quality of a surface topography is the surface roughness, which is represented by the arithmetic mean value, Ra. In this invention disclosure, a rough surface with Ra not less than 0.1 µm or preferably not less than 1 µm when antiblocking agent is used with or without a cold processing temperature, resulted in a non-blocking fecal catheter.

An important characteristic about the formulation described in this invention is its ability to be post-extrusion converted, both by welding and adhesive bonding. Greater than 5 N/in adhesive strength and heat weld strength was achieved.

Another embodiment of the present invention is related to the use of organoclays and/or zeolites to improve the odor barrier of the elastomer catheter. For example, a single layer of catheter can be made from an organoclay-containing elastomer selected from the group consisting of silicone, polyurethane, styrenic block copolymer, thermoplastic vulcanizate, or polyolefin elastomer with a Shore A hardness not more than 60, or more preferably not more than 50.

The use of nanocomposite (nanoclays) fillers to improve the odor barrier is not new. The addition of nanocomposite fillers creates the tortuous path for the odor causing compounds; thus improving the odor barrier for the substrate. There are various nanocomposite containing coating, additives, or polymers marketed by various companies, such as Nanocor, Nanoresin, Southern Clays, Nano-X, Inmat, etc. Since nanocomposites are mostly clay based, it is relatively rigid. Therefore, the challenges of using nanocomposite fillers in FMS application are two fold, (1) the difficulty in the wetting and adhesion of the nanocomposite fillers or coating onto the silicone tubing, and (2) the odor barrier property upon flexing. Therefore, the uniqueness of this invention is the formulation of a soft tube with a completely covered, and/or relatively uniformly dispersed nanocomposite containing catheter which would not crack upon flexing. Such a soft nanoclay-containing catheter is characterized with a Shore A hardness not more than 60, or more preferably not more than 50.

Another embodiment of the present invention is related to single layer of catheter made from a zeolite-containing elastomer selected from the group consisting of silicone, polyurethane, styrenic block copolymer, thermoplastic vulcanizate, or polyolefin elastomer with a Shore A hardness not more than 60, or more preferably not more than 50.

The addition of zeolite creates the tortuous paths and sites to adsorb the odor causing compounds; thus improving the odor barrier for the substrate. There are various zeolites marketed by various companies, such as UOP. Since zeolites are hard fillers, they produce rigidity when used. Therefore, the challenges of using zeolites in FMS application are two fold, (1) the difficulty in the wetting and adhesion of the zeolite coating onto the silicone tubing, and (2) the odor barrier property upon flexing. Therefore, the uniqueness of this invention is the formulation of a soft tube with relatively uniform zeolite-containing elastomeric catheter which would not crack upon flexing. Such a soft zeolite-containing catheter is characterized with a Shore A hardness not more than 60, or more preferably not more than 50.

Another embodiment of the present invention is related to an organoclay-containing coating onto an elastomer substrate selected from the group consisting of silicone, polyurethane, styrenic block copolymer, thermoplastic vulcanizate, or polyolefin elastomer with a Shore A hardness not more than 60, or more preferably not more than 50.

Another embodiment of the present invention is related to a zeolite-containing coating onto an elastomer substrate selected from the group consisting of silicone, polyurethane, styrenic block copolymer, thermoplastic vulcanizate, or polyolefin elastomer with a Shore A hardness not more than 60, or more preferably not more than 50.

A series of experiments were conducted as described below. A total of four different nanocomposites were evaluated, two from Southern Clay and two from Nanocor. Two types of coating matrix were used, silicone and polyurethane. The following is a summary of these findings:

Exp. #1: Silicone Coating Consisting of Nanocomposites 2.5% of the following nanocomposites were added into a two-part silicone made by Nusil 6350, including
(1) Southern Clay Cloisite Na+, Hydrated Aluminum Silicate,
(2) Southern Clay Cloisite 15A, Ammonium salts with Bentonite,
(3) Nanocor 1.30E (Octadecyl ammonium surface compatibilized montmorillonite), and
(4) Nanocor 1.34 TCN (methyl, bis hydroxyethyl octadecyl ammonium surface compatibilized montmorillonite).

The two-part silicone was applied onto the silicone catheter as a coating, and was then heat cured at 130 deg C. for 30 minutes. The coated catheter was then tested for onion odor barrier per ISO 8670-3:2000. About 5 grams of onion was chopped and filled inside a 12 cm long coated silicone tubing (i.e., catheter).

|  | Nanocomposite | | | | |
| --- | --- | --- | --- | --- | --- |
|  | None | Cloisite NA+ | Cloisite 15A | Nanocor 1.30E | Nanocor 1.34TCN |
| Coating Matrix, Nusil 6350 | Silicone | Silicone | Silicone | Silicone | Silicone |
| Substrate, Dow Corning C6-135 | Silicone | Silicone | Silicone | Silicone | Silicone |
| Onset of Onion Smell | 5 minutes | 45 minutes | 45 minutes | 90 minutes | 60 minutes |

As can be seen, the addition of 2.5% nanocomposites in a silicone coating improves the onion odor barrier in the silicone tubing. The control with a silicone coating had an onset of onion odor outside of the closed silicone tubing at around 5 minutes. This is about the same as the silicone tube without any coating. After a silicone coating consisting of 2.5% nanocomposites was applied onto a silicone tube, the onset of the onion odor was extended to 45-90 minutes.

Exp. #2: Polyurethane Coating Consisting of Nanocomposites, without Primer 2.5% of the following nanocomposites were added into a two-part polyurethane made by Smooth-On, Vytaflex 30, including
(1) Southern Clay Cloisite Na+, Hydrated Aluminum Silicate,
(2) Southern Clay Cloisite 15A, Ammonium salts with Bentonite,
(3) Nanocor 1.30E (Octadecyl ammonium surface compatibilized montmorillonite), and
(4) Nanocor 1.34TCN (methyl, bis hydroxyethyl octadecyl ammonium surface compatibilized montmorillonite).

The two-part polyurethane was applied onto the silicone catheter as a coating, and was then room temperature cured for 6 hours. The coated catheter was then tested for onion odor barrier per ISO 8670-3:2000. About 5 grams of onion was chopped and filled inside a 12 cm long coated silicone tubing (i.e., catheter).

|  | Nanocomposite | | | | |
| --- | --- | --- | --- | --- | --- |
|  | None | Cloisite NA+ | Cloisite 15A | Nanocor 1.30E | Nanocor 1.34TCN |
| Coating Matrix, Vytaflex 30 | Polyurethane | Polyurethane | Polyurethane | Polyurethane | Polyurethane |
| Primer, Dow Corning 1200 | No | No | No | No | No |

-continued

|  | Nanocomposite | | | | |
| --- | --- | --- | --- | --- | --- |
|  | None | Cloisite NA+ | Cloisite 15A | Nanocor 1.30E | Nanocor 1.34TCN |
| Substrate, Dow Corning C6-135 | Silicone | Silicone | Silicone | Silicone | Silicone |
| Onset of Onion Smell | 30 minutes | 6 hours | 6 hours | >12 hours | >12 hours |

As can be seen, the addition of 2.5% nanocomposites significantly improves the onion odor barrier. The control with a polyurethane coating, but without any nanocomposites, was able to extend the onset of onion odor outside of the closed silicone tubing from 5 minutes to 30 minutes. After a polyurethane coating consisting of 2.5% nanocomposites was applied onto a silicone tube, the onset of the onion odor was extended to 6-12 hours. Despite of the odor barrier improvement, the coating adhesion was poor.

Exp. #3: Polyurethane Coating Consisting of Nanocomposites, with Primer

The same set of experiment as Exp. #2 was repeated with the use of a silane primer, Dow Corning 1200. The same level of onion odor improvement was observed. That is, after a polyurethane coating consisting of 2.5% nanocomposites was applied onto a silicone tube primed with a silane, the onset of the onion odor was extended from 30 minutes in the control without any nanocomposites to 6-12 hours. The polyurethane coating stuck well to the silicone tube, and was able to resist the flex.

|  | Nanocomposite | | | | |
| --- | --- | --- | --- | --- | --- |
|  | None | Cloisite NA+ | Cloisite 15A | Nanocor 1.30E | Nanocor 1.34TCN |
| Coating Matrix, Vytaflex 30 | Polyurethane | Polyurethane | Polyurethane | Polyurethane | Polyurethane |
| Primer, Dow Corning 1200 | Yes | Yes | Yes | Yes | Yes |
| Substrate, Dow Corning C6-135 | Silicone | Silicone | Silicone | Silicone | Silicone |
| Onset of Onion Smell | 30 minutes | 6.5 hours | 6 hours | >12 hours | >12 hours |

Exp. #4: Nanocomposites in a Silicone Slab

2% of Nanocor 1.30E was added to make into a 1 mm thick (i.e., 40 mil) silicone gel slab, Nusil 6350. Onion barrier was compared on silicone slab with and without the nanocomposite per ISO 8670-3:2000.

|  | 1 mm thick silicone slab without nano-composites (control) | 1 mm thick silicone slab with 2% Nanocor 1.30E |
| --- | --- | --- |
| Onset of Onion Smell | 5-10 minutes | 60 minutes |

As a result, the addition of 2% of Nanocor 1.30E improved the onion odor barrier of the silicone slab from 5 minutes to about 60 minutes.

Another embodiment of the present invention is an improved odor barrier fecal catheter, having a Hardness of less than Shore A 60, comprising at least (a) one layer of a silane coupling agent, and (b) at least one layer of nanocomposite coating. This formulation, when applied onto a silicone fecal catheter, would result in an oxygen transmission rate no more than 20,000 cc/m2/day, or preferably, no more than 10,000 cc/m2/day, or more preferably no more than 5,000 cc/m2/day. A silicone tube without the use of silane coupling agent and without the nanocomposite coating has an oxygen permeation rate of around 37,500 cc/m2/day. A silicone with the nanocomposite coating, but without the silane coupling agent, has an oxygen permeation rate of close to 30,000-35,000 cc/m2/day due to the lack of bonding. Alternatively, the same formulation can be applied onto a thermoplastic elastomer (TPE) or a polyurethane tubing (PU), having a Hardness of less than Shore A 60, such that the gas barrier is improved to no more than 25,000 cc/m2/day, or preferably, no more than 10,000 cc/m2/day, or more preferably no more than 5,000 cc/m2/day.

The materials described in this invention can be used as a fecal catheter. A fecal pouch is commonly connected to a fecal catheter in use. The same materials described for fecal catheter were used to make a fecal pouch. Similar odor barrier characteristics against oxygen transmission and onion odor shown in Table 1 were obtained in the lab. Thus, besides a fecal catheter, the same material construction could be used for an ostomy pouch.

We claim:

1. A soft odor barrier material in a medical device, the soft odor barrier material comprising an elastomer and an anti-blocking agent that imparts an interior rough surface having an arithmetic mean surface roughness (Ra) not less than 0.1 µm.

2. The soft odor barrier material of claim 1, wherein the arithmetic mean surface roughness (Ra) is not less than 1 µm.

3. The soft odor barrier material of claim 1, wherein the odor barrier material is non-blocking upon folding and packaging.

4. The soft odor barrier material of claim 1, wherein the elastomer is selected from the group consisting of a silicone, a polyurethane, a styrenic block copolymer, a thermoplastic vulcanizate, and a polyolefin elastomer.

5. The soft odor barrier material of claim 1, further comprising an odor barrier modifier selected from the group consisting of a polyisobutene, a polybutene, and an organo-clay.

6. The soft odor barrier material of claim 1, wherein the antiblocking agent is selected from the group consisting essentially of inorganic fillers, including silica, talc, clay, and mica, and any combination thereof.

7. The soft odor barrier material of claim 1, wherein the elastomer comprises a styrenic block copolymer comprising styrene-isoprene-styrene (SIS), styrene-butadiene-styrene (SBS), styrene-ethylene/butylene-styrene (SEBS), styrene-ethylene/propylene-styrene (SEPS), and/or any combination thereof.

8. The soft odor barrier material of claim 1, wherein the elastomer comprises a polyolefin elastomer comprising an olefin block copolymer, wherein a crystalline phase of the olefin block copolymer acts as hard blocks and an amorphous block copolymer acts as soft blocks.

9. The soft odor barrier material of claim 1, wherein the elastomer comprises a thermoplastic vulcanizate comprising a blend of a curable rubber and a polyolefin.

10. The soft odor barrier material of claim 9,
(i) wherein the curable rubber is selected from the group consisting of ethylene propylene diene monomer (EPDM), ethylene propylene rubber, santoprene, and blends thereof; or
(ii) wherein the polyolefin is polyethylene and polypropylene, including homopolymers and copolymers thereof.

11. The soft odor barrier material of claim 1, further comprising an odor barrier modifier comprising organoclay, wherein the organoclay comprises montmorillonite clay, smectite clay, intercalated clay, nanoclay, or any combination thereof.

12. The soft odor barrier material of claim 1, comprising an odor barrier that is at least 10 times better than silicone, as measured by oxygen transmission rate.

13. The soft odor barrier material of claim 1, comprising an oxygen transmission rate per ASTM D3985 that is 1000 cc/m2/day or less at 23° C.

14. The soft odor barrier material of claim 1, comprising a Shore A hardness of 60 or less.

15. A soft odor barrier material in a medical device, the soft odor barrier material comprising an elastomer and an antiblocking agent that is non-blocking upon folding and packaging.

16. The soft odor barrier material of claim 15, wherein the antiblocking agent imparts an interior rough surface having an arithmetic mean surface roughness (Ra) not less than 0.1 μm.

17. The soft odor barrier material of claim 15, wherein the antiblocking agent imparts an interior rough surface having an arithmetic mean surface roughness (Ra) not less than 1 μm.

18. The soft odor barrier material of claim 15, wherein the odor barrier material can be bonded with an adhesive having an adhesive strength greater than 5 N/in or heat welded having a weld strength greater than 5 N/in.

19. The soft odor barrier material of claim 15, further comprising a nanocomposite filler material coated on or present within the elastomer so as to provide an odor barrier.

20. The soft odor barrier material of claim 19, wherein the elastomer and the nanocomposite filler form a soft catheter tube having a Shore A hardness of not more than 60.

* * * * *